United States Patent [19]
Drennen et al.

[11] 3,966,408
[45] June 29, 1976

[54] STERILANT IMMERSION CONTAINER WITH COVER ACTUATED TRAY

[76] Inventors: Richard E. Drennen, Fairway Heights; Keith L. Stutzman, 19 N. Seventh, both of Denison, Iowa 51442

[22] Filed: Feb. 13, 1975

[21] Appl. No.: 549,503

[52] U.S. Cl. ........................ 21/87; 21/83; 21/103; 21/105; 134/135; 312/130; 312/272.5; 312/274; 312/276
[51] Int. Cl.² .................. A61L 3/00; A61L 3/02; A47B 81/00
[58] Field of Search ............... 21/83, 86, 100, 1, 87, 21/90, 99, 103, 105; 312/130, 271, 272.5, 273, 274, 276; 134/135; 190/30

[56] References Cited
UNITED STATES PATENTS

| | | | |
|---|---|---|---|
| 1,417,814 | 5/1922 | Fairweather | 312/272.5 |
| 1,697,335 | 1/1929 | Weber | 21/100 |
| 1,850,524 | 3/1932 | Whittaker | 21/87 |
| 1,934,272 | 11/1933 | Miller | 312/272 |
| 3,500,840 | 3/1970 | Maatz | 21/105 |

Primary Examiner—Morris O. Wolk
Assistant Examiner—Dale Lovercheck
Attorney, Agent, or Firm—Henderson, Strom & Sturm

[57] ABSTRACT

A unit for sterilizing instruments in a chemical germicide solution having a container for holding the solution and a cover for closing the container. A tray having slots formed in the bottom thereof receives the instruments. A support for the tray is attached between the cover and the bottom of the container and moves the tray and instruments from a first position of immersion in the solution to a second position above the solution as the cover is pivoted upwardly from the container. The slots in the tray allow the solution to drain from the tray and the instruments.

6 Claims, 6 Drawing Figures

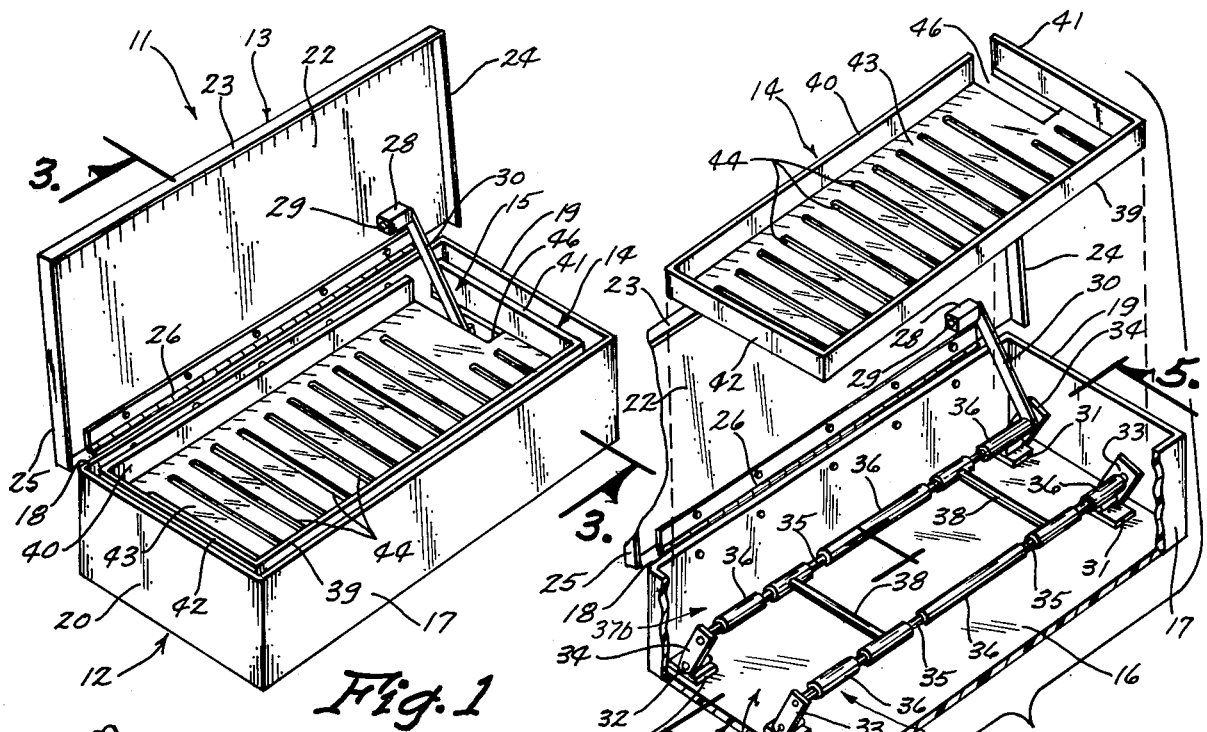
Fig. 1
Fig. 2
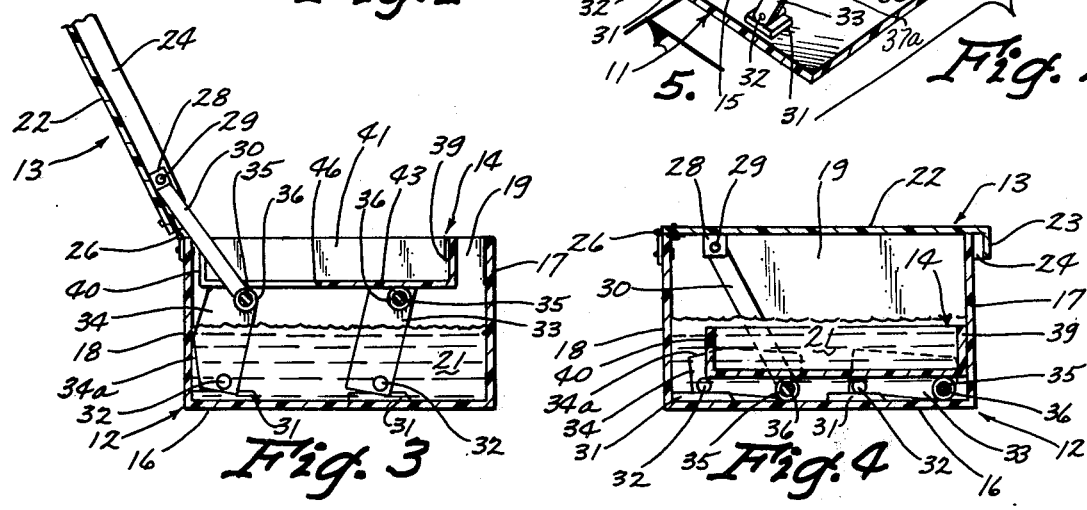
Fig. 3
Fig. 4
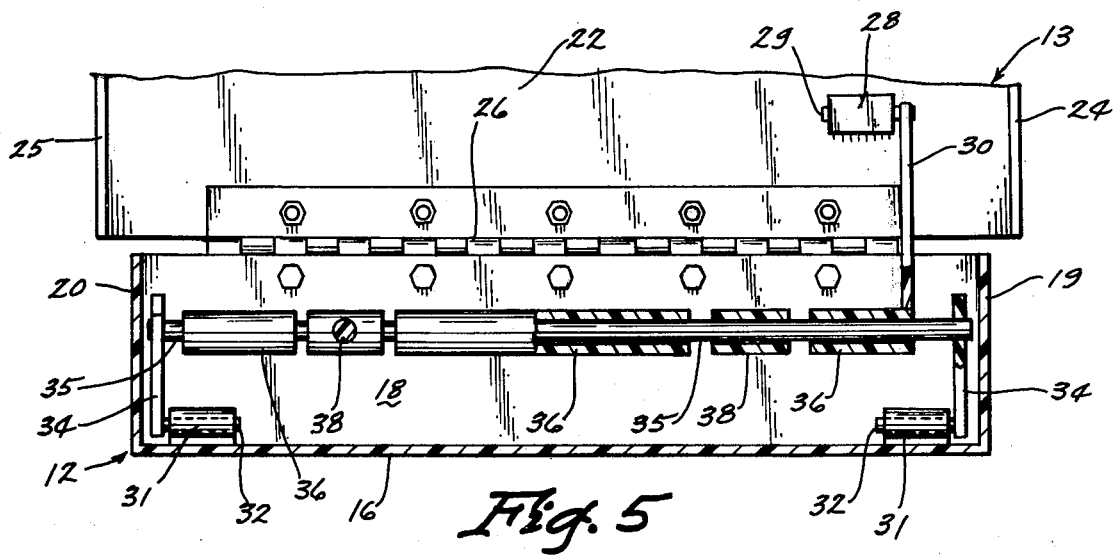
Fig. 5

STERILANT IMMERSION CONTAINER WITH COVER ACTUATED TRAY

BACKGROUND OF THE INVENTION

This invention relates to structures used for sterilization of instruments by physicians, dentists, veterinarians, barbers, beauticians and allied professions where sterilization is a requirement. More particularly, this invention relates to structures used for cold sterilization, the sterilization of instruments in germicide solution.

Structures which have been used for cold sterilization have normally supported the instruments to be sterilized in trays. These trays are immersed in the germicide solution and then elevated above the solution for drying. The trays either have a wire mesh bottom, as in U.S. Pat. No. 1,953,243 to Louvier, U.S. Pat. No. 2,549,160 to Bess and U.S. Pat. No. 3,801,279 to Grieco, or a bottom having circular apertures as in U.S. Pat. No. 2,786,245 to Steinbock. The wire mesh bottoms facilitate drainage but are an inherently fragile type of structure. Structures similar to Steinbock, on the other hand, are stronger but do not have the rapid drainage properties of the wire mesh bottoms.

Cold sterilization structures have also normally supported the instrument tray by suspending it from the lid or cover of the structure, as illustrated by the Grieco patent. Large amounts of wear result to the cover as a result of such an arrangement.

SUMMARY OF THE INVENTION

According to this invention, a cold sterilization unit is provided having a container member suitable for holding a germicide solution. A cover is pivotally attached to the container.

A tray, having a plurality of narrow slots and a wide slot formed therein for permitting both ingress and drainage of the germicide solution, is removably placed upon a structure for supporting and moving the tray. The structure for supporting and moving the tray is interconnected between the cover and the bottom of the container and moves the tray between an immersed position and a position above the solution upon movement of the cover between closed and open positions.

It is an object of this invention to provide a sterilizer unit which is simple yet tough and durable in structure and economical of manufacture.

Another object of this invention is to provide a sterilizer unit of greater durability by having an improved support structure for the instrument bearing tray.

Still another object of this invention is to provide a sterilizer unit with an improved instrument bearing tray having great strength and superior drainage properties.

These objects and other features and advantages of this invention will become readily apparent by reference to the following description when taken in conjunction with the accompanying drawings.

BRIEF DESCRIPTION OF THE DRAWINGS

The appended drawings illustrate the invention, wherein;

FIG. 1 is a perspective view of the sterilizer unit of this invention;

FIG. 2 is a fragmentary perspective and exploded view of the sterilizer unit more clearly depicting the tray and the structure for supporting and moving the tray;

FIG. 3 is a cross-section view taken along line 3—3 of FIG. 1 depicting the tray in the elevated position;

FIG. 4 is cross-section view similar to that of FIG. 3 but showing the tray in the immersed position;

FIG. 5 is an enlarged, fragmentary longitudinal section taken along line 5—5 of FIG. 2.

DESCRIPTION OF THE PREFERRED EMBODIMENT

Figure 6:
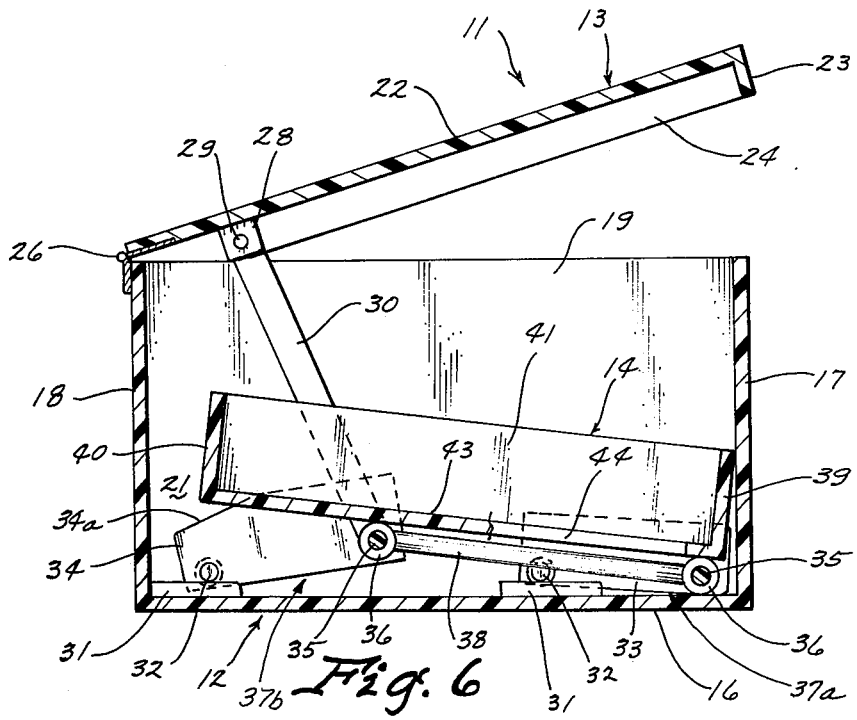
FIG. 6 is an enlarged cross-section view similar to that of FIGS. 3 and 4 but showing the tray in a position angularly disposed to the horizontal as the tray is being moved between the positions depicted in FIGS. 3 and 4.

Referring now to the drawings, the sterilizer unit comprising this invention is indicated generally at 11 in FIG. 1. The sterilizer 11 generally includes a rectangular container 12, a cover 13, a tray 14 and a structure for support and movement 15.

Referring to FIGS. 1 and 2, the container 12 is open-topped and has a bottom portion 16 with front and rear walls 17,18 perpendicularly affixed to opposite edges thereof. Left and right side walls 19,20 are also perpendicularly affixed to opposite edges of the bottom portion 16 and join the walls 17,18 together. A germicide solution 21 is held within the container 12.

Again referring to FIG. 1, the cover 13 includes a main top portion 22 having a depending front 23 and depending left and right sides 24,25. The cover 13 is affixed to the container 12 by a hinge member 26. The hinge 26 is affixed between the rear wall 18 of the container 12 and the rear portion of the top 22 of the cover 13.

The tray 14, most clearly depicted in FIG. 2, includes parallel front and rear sides 39,40 and parallel left and right sides 41,42. The sides 41,42 are perpendicular to and interconnect the sides 39,40. The tray 14 has a bottom portion 43, the sides 39,40,41,42 upstanding therefrom in a perpendicular manner. Uniformly spaced narrow slots 44 are formed in the bottom 43 and are disposed parallel to the sides 41,42. A wide slot 46 is formed, adjacent to the left side 41, in the bottom 43 and through the rear side 40.

The structure for support and movement 15 is most clearly depicted in FIG. 2. A support block 28 is affixed to the top portion 22 near to the hinge 26 and the left side 24 of the cover 13. A pin 29 is rotatably seated in the block 28 and is affixed to one end of a link arm 30. Four support brackets 31 are affixed to the bottom 16 of the container 12, two brackets 31 being aligned and adjacent to the left side wall 19 and two brackets 31 being aligned and adjacent to the right side wall 20. One bracket 31 next to each of the walls 19,20 is also located adjacent to the rear wall 18 of the container 12. Pins 32 are rotatably seated in the brackets 31.

Front and rear support arms 33, 34 are affixed at one end to the pins 32 and are thereby pivotally supported by the brackets 31. The rear support arms 34 have beveled edges 34a. Main shafts 35 are affixed between the front support arms 33 and between the rear support arms 34, the shafts 35 being received by the ends of the support arms 33,34 opposite the ends attached to the pins 32. Sleeves 36 are fitted over the main shafts 35 and are movable along and rotatable about the shafts 35. The front support arms 33, together with the shaft 35 and sleeves 36 supported therebetween, constitute a forwardly disposed first pivot support unit 37a, while the rear support arms 34 with a shaft 35 and sleeves 36 supported therebetween constitute a rearwardly disposed second pivot support unit 37b. Sleeved cross-support members 38 are fitted over the shafts 35 and interconnect the first and second pivot support units 37a, 37b. The link arm 30 is attached to a sleeve 36 of the second pivot support 37b. The tray 14 rests upon the sleeves 36 of the pivot supports 37a,37b and is removable therefrom, and the link arm 30 is received within the slot 46.

When the sterilizer unit 11 is in operation, the cover 13 is pivoted to the position depicted in FIGS. 1 and 3, and the germicide solution 21 is placed within the container 12. The removable tray 14 is placed upon the sleeve 36 of the structure for support and movement 15, and the instruments to be sterilized (not shown) are placed in the tray 14. The tray 14 is in the horizontally disposed elevated position above the solution 21 depicted in FIG. 3. The cover 13 is then pivoted to the closed position depicted in FIG. 4, the lever arm 30 being actuated by the cover 13 to pivot the structure for support and movement 15 toward the front wall 17 of the container 12, thereby moving the tray 14 to the horizontally disposed position of immersion within the solution 21. The link arm 30 then forms an acute angle with the rear support arms 34.

When it is desired to remove an instrument(s) (not shown) from the sterilizer unit 11, the cover 13 is pivoted upwardly from the position depicted in FIG. 4 to the position shown in FIG. 3. The link arm 30 is lifted by the cover 13, and in turn the link arm 30, through the attached sleeve 36, FIG. 5, lifts the main shaft 35, thereby causing the second pivot support 37b to pivot upwardly and rearwardly. The tray 14 is thereby made angularly disposed to the horizontal, as depicted in FIG. 6.

When the link arm 30 and the rear support arms 34 form a right angle, the second pivot support 37b, through the sleeved cross-support members 38, begins to pivot the first pivot support 37a upwardly, rearwardly and in parallel relation to the second pivot support 37b. As the pivot supports 37a,37b are moved to the upright position shown in FIG. 3, the tray 14 is moved into a horizontally disposed position again. The rocking of the tray 14 actively moves the solution 21 caught in the tray 14 over the slots 44,46, thereby aiding the drainage of the tray 14 and instruments (not shown). The parallel slots 44, in addition to enabling drainage of the tray 14, prevent the instruments (not shown) from rolling against the link arm 30 or through the wide slot 46. The beveled edge 34a moves against the rear wall 18 of the container 2, thereby preventing pivoting of the cover 13 beyond the position depicted in FIG. 3.

When the instruments (not shown) have drained, they may be removed, or, alternately, the tray 14 may be removed. When the solution 21 is to be changed, the tray 14 is removed, and the container 12 is tipped to pour out the old solution 21. Pads (not shown) may be affixed to the bottom 16 to prevent the sterilizer unit 11 from sliding along the surface upon which it is resting.

The braking and supporting actions of the rear support arms 34 with beveled edges 34a, and the supporting actions of the pivot support units 37a,37b result in less wear to the cover 13 and link arm 30. The parallel slots 44 result in a tray 14 having rapid self-draining properties and a bottom 43 having great strength. The sterilizer unit 11 thereby is made very durable. Thus it can be seen that the objects of this invention have been attained.

Although a preferred embodiment has been disclosed herein, is is to be remembered that various modifications and alternate constructions can be made thereto without departing from the full scope of the invention, as defined in the appended claims.

I claim:

1. For effecting the sterilization of instruments in a chemical germicide solution, a sterilizer unit comprising:
   a container member having a bottom and walls, said walls being joined in end to end fashion and being perpendicularly attached to said bottom, said walls forming an opening, the germicide solution being received through said opeing and held by said walls and said bottom;
   a cover member pivotally attached to said container and movable to close said opening of said container;
   a removable tray member having a wide slot and a plurality of narrow slots formed therethrough, said wide slot and said narrow slots being disposed in parallel with respect to each other, the instruments being received and held by said tray;
   means for supporting, rocking and moving said tray between a first position adjacent said bottom and a second position adjacent said opening, said tray being supported in a horizontally disposed manner at both said first and said second positions, said tray being immersed in the germicide solution at said first position and being elevated above the germicide solution at said second position, the germicide solution draining from said tray through said wide and narrow slots into said container when said tray is in said second position, said tray being rocked through dispositions at an angle to the horizontal while between said first and said second positions, said means for supporting, rocking and moving including first and second pivot support units and at least one cross member, both of said pivot support units being pivotally attached to said bottom of said container, said cross member interconnecting said pivot support units, said tray resting upon said pivot support units; and
   means connecting said cover member and said means for supporting, rocking and moving, for moving said means for supporting, rocking and moving in response to movement of said cover member, said connecting means for moving being received within said wide slot.

2. A sterilizer unit as defined in claim 1 and further wherein both said first and said second pivot support units include a shaft member, spaced apart support arms, and a plurality of sleeve members, each support arm being pivotally attached to said bottom of said container and extending therefrom to attachment with said shaft, each sleeve member being fitted over said shaft and movable thereon between said support arms, said tray resting upon said sleeves.

3. A sterilizer unit as defined in claim 2 and further wherein said support arms of said second pivot support unit have a beveled edge movable against said walls of said container when said tray is held in said second position, whereby said means for supporting, rocking and moving is braked against further movement.

4. A sterilizer unit as defined in claim 2 and further wherein said slots are perpendicular to said shafts when said tray is resting upon said sleeves.

5. A sterilizer unit as defined in claim 2 and further wherein said connecting means includes a link arm which initially pivots only said second pivot support unit thereby orienting said tray at an angle to the horizontal, said link arm pivoting both pivot support units upon attaining a perpendicular relationship to said support arms of said second pivot support unit, said tray being reoriented to a horizontal disposition at said second position, whereby a rocking motion is imparted to said tray to positively move the germicide solution over said slots thereby accelerating draining of the germicide solution from the instruments.

6. A sterilizer unit as defined in claim 5 and further wherein said means for supporting, rocking and moving includes a plurality of uniformly spaced cross members, each cross member having sleeved ends fitted over said shafts, said cross members extending between said shafts and being slideable along said shafts.

* * * * *